(12) United States Patent
Jones et al.

(10) Patent No.: US 7,247,021 B2
(45) Date of Patent: **\*Jul. 24, 2007**

(54) SUBDIVIDING A DIGITAL DENTITION MODEL

(75) Inventors: Timothy N. Jones, Mountain View, CA (US); Muhammad Chishti, Washington, DC (US); Huafeng Wen, Redwood Shores, CA (US); Gregory Bala, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/802,124

(22) Filed: Mar. 15, 2004

(65) Prior Publication Data
US 2004/0175671 A1    Sep. 9, 2004

Related U.S. Application Data

(63) Continuation of application No. 09/264,547, filed on Mar. 8, 1999, now Pat. No. 7,063,532, which is a continuation-in-part of application No. 09/169,276, filed as application No. PCT/US98/12861 on Jun. 19, 1998, now abandoned.

(60) Provisional application No. 60/050,342, filed on Jun. 20, 1997.

(51) Int. Cl.
*A61C 11/00* (2006.01)
*A61C 3/00* (2006.01)

(52) U.S. Cl. .......................... 433/213; 433/24
(58) Field of Classification Search .............. 433/24, 433/213
See application file for complete search history.

(56) References Cited

U.S. PATENT DOCUMENTS 2,467,432 A    4/1949    Kesling (Continued)

FOREIGN PATENT DOCUMENTS

AU    3031677    5/1979

(Continued)

OTHER PUBLICATIONS

*ARS Materials, Inc., Technical Magazine*, http://www.essix.com/magazine/default.html, Aug. 1997, 7 pgs.

(Continued)

*Primary Examiner*—John J Wilson
(74) *Attorney, Agent, or Firm*—Townsend and Townsend and Crew LLP

(57) ABSTRACT

A computer or other digital circuitry is used to assist in the creation of a digital model of an individual component, such as a tooth or gum tissue, in a patient's dentition. The computer receives a data set that forms a three-dimensional (3D) representation of the patient's dentition, applies a test to the data set to identify data elements that represent portions of the individual component, and creates a digital model of the individual component based upon the identified data elements. Many implementations require the computer to identify data elements representing a 2D cross-section of the dentition lying in a 2D plane that is roughly parallel to or roughly perpendicular to the dentition's occlusal plane. The computer analyzes the 2D cross-section to identify dentition features that represent boundaries between individual dentition components.

25 Claims, 14 Drawing Sheets

U.S. PATENT DOCUMENTS

| | | | |
|---|---|---|---|
| 3,407,500 A | 10/1968 | Kesling |
| 3,660,900 A | 5/1972 | Andrews |
| 3,683,502 A | 8/1972 | Wallshein |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Mártz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A * | 10/1996 | Mushabac ............... 433/215 |
| 5,587,912 A | 12/1996 | Andersson et al. |
| 5,605,459 A | 2/1997 | Kuroda et al. |
| 5,607,305 A | 3/1997 | Andersson et al. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Dolyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1* | 5/2002 | Poirier ............... 433/173 |
| 6,398,548 B1 | 6/2002 | Muhammad et al. |
| 6,524,101 B1 | 2/2003 | Phan et al. |
| 6,554,611 B2 | 4/2003 | Chishti et al. |
| 2002/0006597 A1 | 1/2002 | Andreiko et al. |

FOREIGN PATENT DOCUMENTS

| | | |
|---|---|---|
| AU | 517102 | 7/1981 |
| AU | 5598894 | 6/1994 |
| CA | 1121955 | 4/1982 |

| | | |
|---|---|---|
| DE | 2749802 | 5/1978 |
| DE | 69327661 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0667753 | 8/1995 |
| EP | 0774933 B1 | 5/1997 |
| EP | 0541500 A1 | 6/1998 |
| EP | 0731673 B1 | 9/1998 |
| ES | 463897 | 1/1980 |
| FR | 2 369 828 | 6/1978 |
| FR | 2369828 A1 | 6/1978 |
| FR | 2652256 A1 | 3/1991 |
| GB | 1550777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 | 5/1994 |
| WO | WO 94/10935 A1 | 5/1994 |
| WO | WO 98/32394 | 7/1998 |
| WO | WO 98/44865 A1 | 10/1998 |
| WO | WO 98/58596 A1 | 12/1998 |

OTHER PUBLICATIONS

Biostar Operation & Training Manual, Great Lakes Orthodontics, Ltd., 20 pgs.
Chiappone, Constructing the Gnathologic Setup and Positioner, *J. Clin. Orthod.*, vol. 14, No. 2, Feb. 1980, pp. 121-133.
Cottingham, Gnathologic Clear Plastic Positioner, *Am.J.Orthod.*, vol. 55, No. 1, Jan. 1969, pp. 23-31.
Cureton, Correcting Malaligned Mandibular Incisors with Removable Retainers, *IC/in. Orthod.*, vol. 30, No. 7, Jul. 1996, pp. 390-395.
Elsasser, Some Observations on the History and Uses of the Kesling Positioner, *Am. J. Orthod.*, vol. 36, 1-12/50, pp. 368-374.
Kamada et al., Construction of Tooth Positioners with LTV Vinyl Silicone Rubber and Some Case Reports,*J. Nihon University School of Dentistry*, vol. 24, No. 1, Mar. 1982, pp. 1-27.
Kesling, Coordinating the Predetermined Pattern and Tooth Positioner with Conventional Treatment, *Am. J. Orthod. Oral. Surg.*, vol. 32, No. 5, May 1946, pp. 285-293.
Kesling, the Philosophy of the Tooth Positioning Appliance, *Am. J. Orthod. Oral. Surg.*, vol. 31, No. 6, Jun. 1945, pp. 297-304.
Kleeman et al., The Speed Positioner, *J. Clin. Orthod.*, vol. 30, No. 12, Dec. 1996, pp. 673-680.
Kuroda et al., Three-dimensinal Dental Cast Analyzing System Using Laser Scanning, *Am. J. Orthod Dentofac.*, vol. 110, No. 4, Oct. 1996, pp. 365-369.
Resin (Orthocon), *Nippon Dental Review*, vol. 452, Jun. 1980, pp. 61-74.
Sheridan, Moving Teeth with Essix™ Appliances: Windows & Divots™, *Essix™ Appliances, Fabrication, Application and Rationale*, Raintree Essix&.
Shilliday, Minimizing Finishing Problems with the Mini-positioner, *Am. J. Orthod* vol. 59, No. 6 Jun. 1971, pp. 596-599.
Warunek et al., Physical and Mechanical Properties of Elastomers in Orthodontic Positioners, *Am. J. Orthod. Dentofac. Orthop.* vol. 95, No. 5, May 1989, pp. 388-400.
Wells, Application of the Positioner Appliance in Orthodontic Treatment, *Am. J. Orthodont.* vol. 58, No. 4, Oct. 1970, pp. 351-366.
Yoshii, Research on a New Orthodontic Appliance: The Dynamic Positioner (D.P.)-I. The D.P. Concept and Implementation of Transparent Silicone.
Yoshii, Research on a New Orthodontic Appliance: The Dynamic Positioner (D.P.)-II. The D.P. Manufacturing Procedure and Cinical Applications, Nippon Dental Review, vol. 454, Aug. 1980, pp. 107-130.
Yoshii, Research on a New Orthodontic Appliance: The Dynamic Positioner (D.P.)-III. The General Concept of the D.P. Method and its Therapeutic Effect, Part 1. Dental and Functional Reversed Occlusion Case Reports, Nippon Dental Review, vol. 457, Nov. 1980, pp. 146-164.
Yoshiki, Research on a New Orthodontic Appliance: The Dynamic Positioner (D.P.)-III. The General Concept of the D.P. Method and its Therapeutic, Effect, Part 2. Skeletal Reversed Occlusion Case Reports, Nippon Dental Review, vol. 458, Dec. 1980, pp. 112-129.
Alexander et al., "The DigiGraph Work Station Part 2, Clinical Management," *JCO*(Jul. 1990), pp. 402-407.
Altschuler et al, "Measuring Surfaces Space-Coded by a Laser-Projected Dot Matrix," *SPIE Imaging Applications for Automated Industrial Inspection and Assembly*, vol. 182 (1979), p. 187-191.
Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.
Altschuler et al., "Laser Electro-Optic System for Rapid Three-Dimensional (3D) Topographic Mapping of Surfaces," *Optical Engineering*, vol. 20(6) (1981), pp. 953-961.
Altschuler, "3D Mapping of Maxillo-Facial Prosthesis," AADR Abstract #607, 1980, 1 page total.
American Association for Dental Research, Summary of Activities, Mar. 20-23, 1980, Los Angeles, CA, p. 195.
Andersson et al., "Clinical Results with Titanium Crowns Fabricated with Machine Duplication and Spark Erosion," *Acta Odontological Scandinavia*, vol. 47 (1989), pp. 279-286.
Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.
Baumrind et al., Mapping the Skull in 3-D, Reprinted from The Journal, *California Dental Association*, vol. 48, No. 2 (1972 Fall Issue) 11 pages total.
Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.
Baumrind, "Integrated Three-Dimensional Craniofacial Mapping: Background, Principles, and Perspectives," *Seminars in Orthodontics*, vol. 7, No. 4 (Dec. 2001), pp. 223-232.
Begole et al., "A Computer System for the Analysis of Dental Casts," *The Angle Orthodontist*, vol. 51 No. 3 (Jul. 1981), pp. 253-259.
Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.
Bhatia et al., "A Computer-Aided Design for Orthognathic Surgery," *British Journal of Oral and Maxillofacial Surgery*, vol. 22 (1984), pp. 237-253.
Biggerstaff et al., "Computerized Analysis of Occlusion In The Postcanine Dentition," *American Journal of Orthodontics*, vol. 61, No. 3, (Mar. 1972), pp. 245-254.
Biggerstaff, "Computerized Diagnostic Setups and Simulations," *The Angle Orthodontist*, vol. 40, No. 1 (Jan. 1970), pp. 28-36.
Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.
Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.
Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.
Burstone (interview), "Dr. Charles J. Burstone on The Uses of the Computer in Orthodontic Practice (Parts1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO*(Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner"*Am. J. Orthod.*, vol. 55, No. 1, (Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bytes" The Computer Moves From The Front Desk To The Operatory, *Canadian Dental Journal*, vol. 54(9), (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9, (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD/CAM in Dentistry," *Journal of the American Dental Association*, vol. 117 (Nov. 1988), pp. 715-720.

Duret et al., "CAD/CAM Imaging In Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery,"Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Ficial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery,"*JCO*, (Apr. 1989), pp. 262-28.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3, (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro," *Schwizerische Monatsschrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz," Invisible Retainers", *Am. J. Orthodontics*, vol. 59, No. 3, Mar. 1971, pp. 266-272.

Procera Research Projects, *PROCERA Research Projects 1993*—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast in Three Dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg* vol. 114 (Apr. 1988), pp. 438-442.

Shilliday, "Minimizing finishing problems with the mini-positioner" *Am. J. Orthod.* 59:596-599, 1971.

Siemens, "CEREC—Computer-Reconstruction," High Tech In der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1100.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse engineering of geometric models—an introduction. Computer-Aided Design, 29 (4):255-268, 1997.

Warunek et al., "Clinical use of silicone elastomer appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging In Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis Of Three-Dimensional Tooth Movement in Orthodontics," *Frontiers in Med. and Biol. Eng'g*, vol. 1, No. 2 (1988), pp. 119-130.

Andrews, *The Six Keys to Optimal Occlusion Straight Wire*, Chapter 3, pp. 13-24.

Bernard et al., Computerized Diagnosis in Orthodontics for Epidemiological Studies: A Progress Report, Paper presented at International Association for Dental Research 66th General Session, Mar. 9-13, 1988, Montreal, Canada. The abstract is published in *J Dental Res Special Issue* vol. 67, p. 169.

Cardinal Industrial Finishes, Powder Coatings information posted at http://www.cardinalpaint.com on Aug. 25, 2000, 2 pages total.

DENT-X posted at http://www.dent-x.com/DentSim.htm Sep. 24, 1998, 6 pages total.

Doyle, Digital Dentistry, *Computer Graphics World*, Oct. 2000 pp. 50-52, 54.

Fütterling et al., "Automated Finite Element Modeling of a Human Mandible with Dental Implants," *WSCG '98—Conference Program*, retrieved from the Internet: <<http://wscg.zcu.cz/wscg98/papers98/Strasser_98.pdf.>>, 8 pages total.

Gottleib et al., "JCO Interviews Dr. James A. McNamura, Jr., on the Frankel Appliance: Part 2: Clinical Management," *Journal of Clinical Orthodontics*, vol. 16, No. 6, (Jun. 1982) pp. 390-407.

Hojjatie et al., "Three-Dimensional Finite Element Analysis of Glass-Ceramic Dental Crowns," *J Biomech.* (1990) vol. 23, No. 11, pp. 1157-1166.

Kunii et.al., Articulation Simulation for an Intelligent Dental Care System, *Displays* (1994) 15:181-188.

Tru-Tain Orthodontic & Dental Supplies, Product Brochure, Rochester, Minnesota 55902, [Not Dated], 16 pages total.

Proffit et al, *Contemporary Orthodontics* (Second Ed.) Chapter 15, Mosby Inc, (Oct. 1992), pp. 470-533.

Raintree Essix & ARS Materials, Inc., Raintree Essix, Technical Magazine Table of contents and Essix Appliances, httpz;//www.essix.com/magazine/default.html Aug. 13, 1997, 7 pages.

Redmond et al. Clinical Implications of Digital Orthodontics, *Am. J. Orthodont. Dentofacial Orthopedics*, vol. 117 No. 2 (2001), pp. 240-242.

Rekow et al., "CAD/CAM for Dental Restorations—Some of the Curious Challenges," *IEEE Transactions on Biomedical Engineering*, (Apr. 1991) vol. 38, No. 4, pp. 344-345.

Rekow et al., "Comparison of Three Data Acquisition Techniques for 3-D Tooth Surface Mapping," *Annual International Conference of the IEEE Engineering in Medicine and Biology Society*, (1991) vol. 13, No. 1, pp. 344-345.

Schroeder et al., Eds. The Visual Toolkit, Prentice Hall PTR, New Jersey (1998) Chapters 6, 8 & 9, (pp. 153-210,309-354, and 355-428, respectively).

Sinclair, "The Readers' Corner," *Journal of Clinical Orthodontics*, vol. 26, No. 6, (Jun. 1992) pp. 369-372.

Varady et al., Reverse Engineering Of Geometric Models—An Introduction, *Computer-Aided Design*, 29 (4):255-268, 1997.

\* cited by examiner

SUBDIVIDING A DIGITAL DENTITION MODEL

CROSS-REFERENCES TO RELATED APPLICATIONS

The present application is a continuation of U.S. application Ser. No. 09/264,547, filed Mar. 8, 1999, now U.S. Pat. No. 7,063,532, which is a continuation-in-part of U.S. application Ser. No. 09/169,276, filed on Oct. 8, 1998, (now abandoned), and entitled "Computer Automated Development of an Orthodontic Treatment Plan and Appliance," which is a continuation-in-part of PCT Application No. PCT/US98/12861, filed on Jun. 19, 1998, and entitled "Method and System for Incrementally Moving Teeth", which is a continuation-in-part of U.S. application Ser. No. 08/947,080, filed on Oct. 8, 1997, and entitled "Method and System for Incrementally Moving Teeth" (now U.S. Pat. No. 5,975,893), which claims the benefit of U.S. Provisional Application No. 60/050,342, filed on Jun. 20, 1997, all of which are incorporated by reference into this application.

BACKGROUND OF THE INVENTION

1. Field of the Invention

The invention relates generally to the fields of dentistry and orthodontics and, more particularly, to subdividing a digital model of a patient's dentition.

Two-dimensional (2D) and three-dimensional (3D) digital image technology has recently been tapped as a tool to assist in dental and orthodontic treatment. Many treatment providers use some form of digital image technology to study the dentitions of patients. U.S. patent application Ser. No. 09/169,276, incorporated by reference above, describes the use of 2D and 3D image data in forming a digital model of a patient's dentition, including models of individual dentition components. Such models are useful, among other things, in developing an orthodontic treatment plan for the patient, as well as in creating one or more orthodontic appliances to implement the treatment plan.

BRIEF SUMMARY OF THE INVENTION

The inventors have developed several computer automated techniques for subdividing, or segmenting, a digital dentition model into models of individual dentition components. These dentition components include, but are not limited to, tooth crowns, tooth roots, and gingival regions. The segmentation techniques include both human assisted and fully automated techniques. Some of the human assisted techniques allow a human user to provide "algorithmic hints" by identifying certain features in the digital dentition model. The identified features then serve as a basis for automated segmentation. Some techniques act on a volumetric 3D image model, or "voxel representation," of the dentition, and other techniques act on a geometric 3D model, or "geometric representation."

In one aspect, a computer implementing the invention receives a data set that forms a three-dimensional (3D) representation of the patient's dentition, applies a test to the data set to identify data elements that represent portions of the individual component, and creates a digital model of the individual component based upon the identified data elements. Some implementations require the computer to identify data elements that form one or more 2D cross-sections of the dentition in one or more 2D planes intersecting the dentition. In many of these embodiments, these 2D planes are roughly parallel to the dentition's occlusal plane. The computer analyzes the features of the 2D cross-sections to identify data elements that correspond to the individual component to be modeled. For example, one technique requires the computer to identify cusps in the 2D cross-sectional surface of the dentition, where the cusps represent the locations of an interproximal margin between teeth in the dentition. One variation of this technique allows the computer to confine its search for cusps in one 2D plane to areas in the vicinity of cusps already identified on another 2D plane. Another variation allows the computer to link cusps on adjacent 2D planes to form a solid surface representing the interproximal margin. Some embodiments allow the computer to receive input from a human user identifying the cusp locations in one or more of the 2D cross sections.

Other embodiments require the computer to identify data elements that represent a structural core, or skeleton, of each individual component to be modeled. The computer creates the model by linking other data elements representing the individual component to the structural core.

In another aspect, a computer implementing the invention receives a three-dimensional (3D) data set representing the patient's dentition, applies a test to identify data elements that represent an interproximal margin between two teeth in the dentition, and applies another computer-implemented test to select data elements that lie on one side of the interproximal margin for inclusion in the digital model. Some implementations require the computer to identify data elements that form one or more 2D cross-sections of the dentition in one or more 2D planes intersecting the dentition roughly parallel to the dentition's occlusal plane.

In another aspect, a computer implementing the invention receives a 3D data set representing at least a portion of the patient's dentition, including at least a portion of a tooth and gum tissue surrounding the tooth; applies a test to identify data elements lying on a gingival boundary that occurs where the tooth and the gum tissue meet; and applies a test to the data elements lying on the boundary to identify other data elements representing portions of the tooth.

Other embodiments and advantages are apparent from the detailed description and the claims below.

DETAILED DESCRIPTION OF THE INVENTION

U.S. patent application Ser. No. 09/169,276 describes techniques for generating a 3D digital model of a patient's dentition, including the crowns and roots of the patients teeth as well as the surrounding gum tissue. One such technique involves creating a physical model of the dentition from a material such as plaster and then digitally imaging the model with a laser scanner or a destructive scanning system. The described techniques are used to produce a volumetric 3D image model ("volume element representation" or "voxel representation") and a geometric 3D surface model ("geometric model") of the dentition. The techniques described below act on one or both of these types of 3D dentition models. In creating a voxel representation, the physical model is usually embedded in a potting material that contrasts sharply with the color of the model to enhance detection of the dentition features. A white dentition model embedded in a black potting material provides the sharpest contrast. A wide variety of information is used to enhance the 3D model, including data taken from photographic images, 2D and 3D x-rays scans, computed tomography (CT) scans, and magnetic resonance imaging (MRI) scans of the patient's dentition.

Figure 1A:
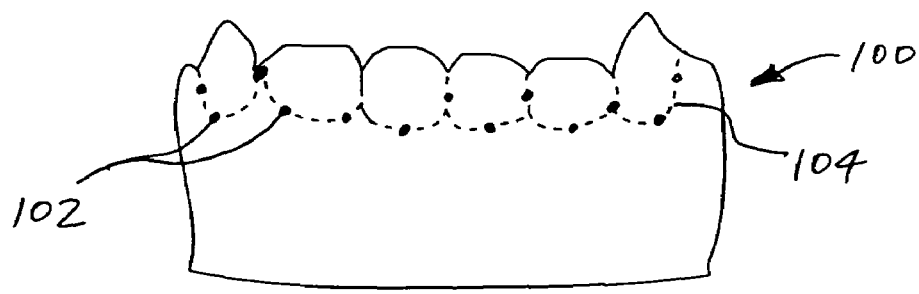
FIGS. 1A, 1B, and 2 are partial views of a dentition model as displayed on a computer monitor and segmented with a human operated saw tool.
Figure 1B:
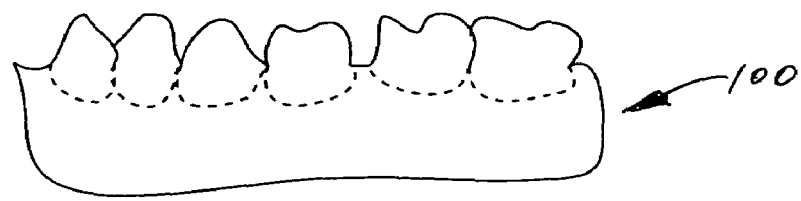
Figure 2:
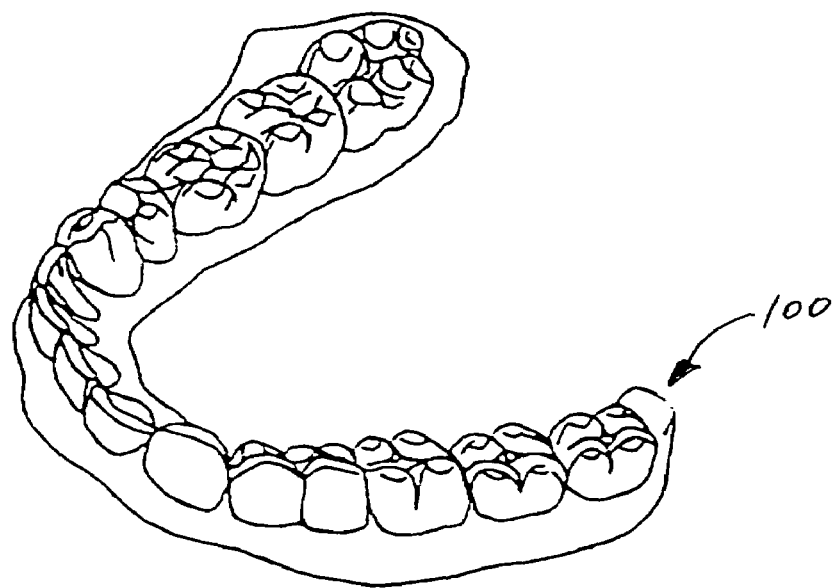

Some computer-implemented techniques for segmenting a 3D dentition model into models of individual dentition components require a substantial amount of human interaction with the computer. One such technique, which is shown in FIGS. 1A, 1B, and 2, provides a graphical user interface with a feature that imitates a conventional saw, allowing the user to identify components to be cut away from the dentition model 100. The graphical user interface provides a rendered 3D image 100 of the dentition model, either at one or more static views from predetermined positions, as shown in FIGS. 1A and 1B, or in a "full 3D " mode that allows the user to alter the viewing angle, as shown in FIG. 2. The saw tool is implemented as a set of mathematical control points 102, represented graphically on the rendered image 100, which define a 3D cutting surface 104 that intersects the volumetric or geometric dentition model. The computer subdivides the data elements in the dentition model by performing a surface intersection operation between the 3D cutting surface 104 and the dentition model. The user sets the locations of the mathematical control points, and thus the geometry and position of the 3D cutting surface, by manipulating the control points in the graphical display with an input device, such as a mouse. The computer provides a visual representation 104 of the cutting surface on the display to assist the user in fitting the surface around the individual component to be separated. Once the intersection operation is complete, the computer creates a model of the individual component using the newly segmented data elements.

Figure 3:
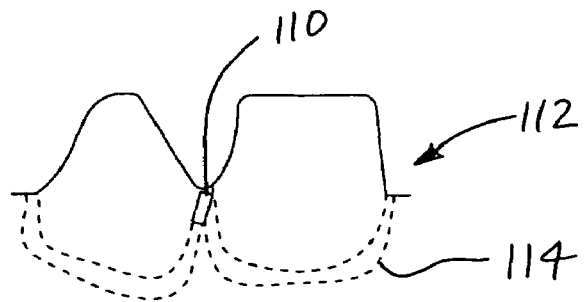
FIG. 3 is a partial view of a dentition model as displayed on a computer monitor and segmented with a human operated eraser tool.

Another technique requiring substantial human interaction, shown in FIG. 3, is a graphical user interface with a tool that imitates a conventional eraser. The eraser tool allows the user to isolate an individual dentition component by removing portions of the dentition model that surround the individual component. The eraser tool is implemented as a 3D solid 110, typically having the shape of a rectangular prism, or a curved surface that matches the shape of a side surface of a tooth. The solid is made as small as possible, usually only a single voxel thick, to minimize degradation of the data set. As with the saw technique above, the graphical user interface presents the user with a rendered 3D image 112 of the dentition model at one or more predetermined static views or in a full 3D mode. The user identifies portions of the dentition model for removal by manipulating a graphical representation 110 of the 3D solid with an input device. In alternative embodiments, the computer either removes the identified portions of the dentition model as the user moves the eraser 112, or the computer waits until the user stops moving the eraser and provides an instruction to remove the identified portions. The computer updates the display in real time to show the path 114 of the eraser through the dentition model.

Figure 4:
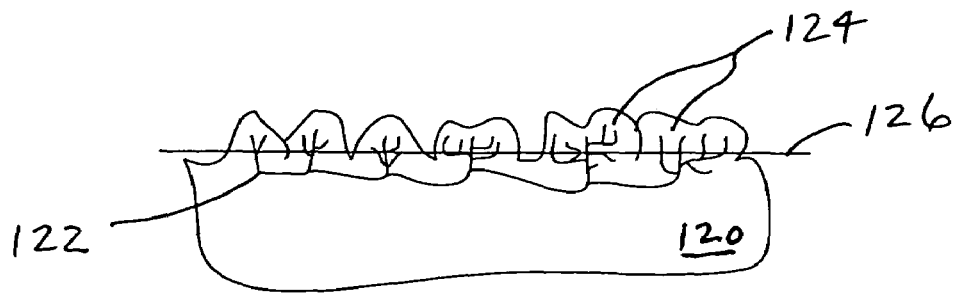
FIG. 4 is a view of a dentition model for which a feature skeleton has been identified.

Other computer-implemented segmentation techniques require little or no human interaction during the segmentation process. One such technique, which is illustrated in FIG. 4, involves the application of conventional "feature skeleton" analysis to a volumetric representation of the dentition model. This technique is particularly useful in identifying and modeling individual teeth. In general, a computer applying this technique identifies a core of voxels, that forms a skeleton 122 for the dentition 120. The skeleton 122 roughly resembles the network of biological nerves within patient's teeth. The computer then divides the skeleton 122 into branches 124, each containing voxels that lie entirely within one tooth. One technique for identifying the branches is by defining a plane 126 that cuts through the skeleton 122 roughly parallel to the occlusal plane of the patient's dentition ("horizontal plane"). Each branch 124 intersects the horizontal plane 126 at one or more points, or clusters, that are relatively distant from the clusters associated with the other branches. The computer forms the individual tooth models by linking other voxels to the appropriate branches 124 of the skeleton.

Figure 5:
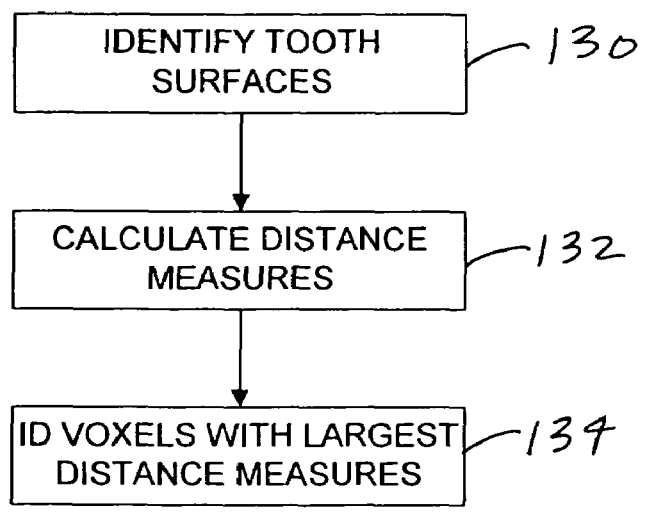
FIGS. 5 and 6 are flow diagram for a feature skeleton analysis technique used in segmenting a dentition model.

FIG. 5 describes a particular technique for forming a skeleton in the dentition model. The computer first identifies the voxels in the dentition model that represent the tooth surfaces (step 130). For a voxel representation that is created from a physical model embedded in a sharply contrasting material, identifying the tooth surfaces is as simple as identifying the voxels at which sharp changes in image value occur, as described in U.S. patent application Ser. No. 09/169,276. The computer then calculates, for each voxel in the model, a distance measure indicating the physical distance between the voxel and the nearest tooth surface (step 132). The computer identifies the voxels with the largest distance measures and labels each of these voxels as forming a portion of the skeleton (step 134). Feature skeleton analysis techniques are described in more detail in the following publications: (1) Gagvani and Silver, "Parameter Controlled Skeletons for 3D Visualization," Proceedings of the IEEE Visualization Conference (1997); (2) Bertrand, "A Parallel Thinning Algorithm for Medial Surfaces," Pattern Recognition Letters, v. 16, pp. 979–986 (1995); (3) Mukherjee, Chatteiji, and Das, "Thinning of 3-D Images Using the Safe Point Thinning Algorithm (SPTA)," Pattern Recognition Letters, v. 10, pp. 167–173 (1989); (4) Niblack, Gibbons, and Capson, "Generating Skeletons and Centerlines from the Distance Transform," CVGIP: Graphical Models and Image Processing, v. 54, n. 5, pp. 420–437 (1992).

Figure 6:
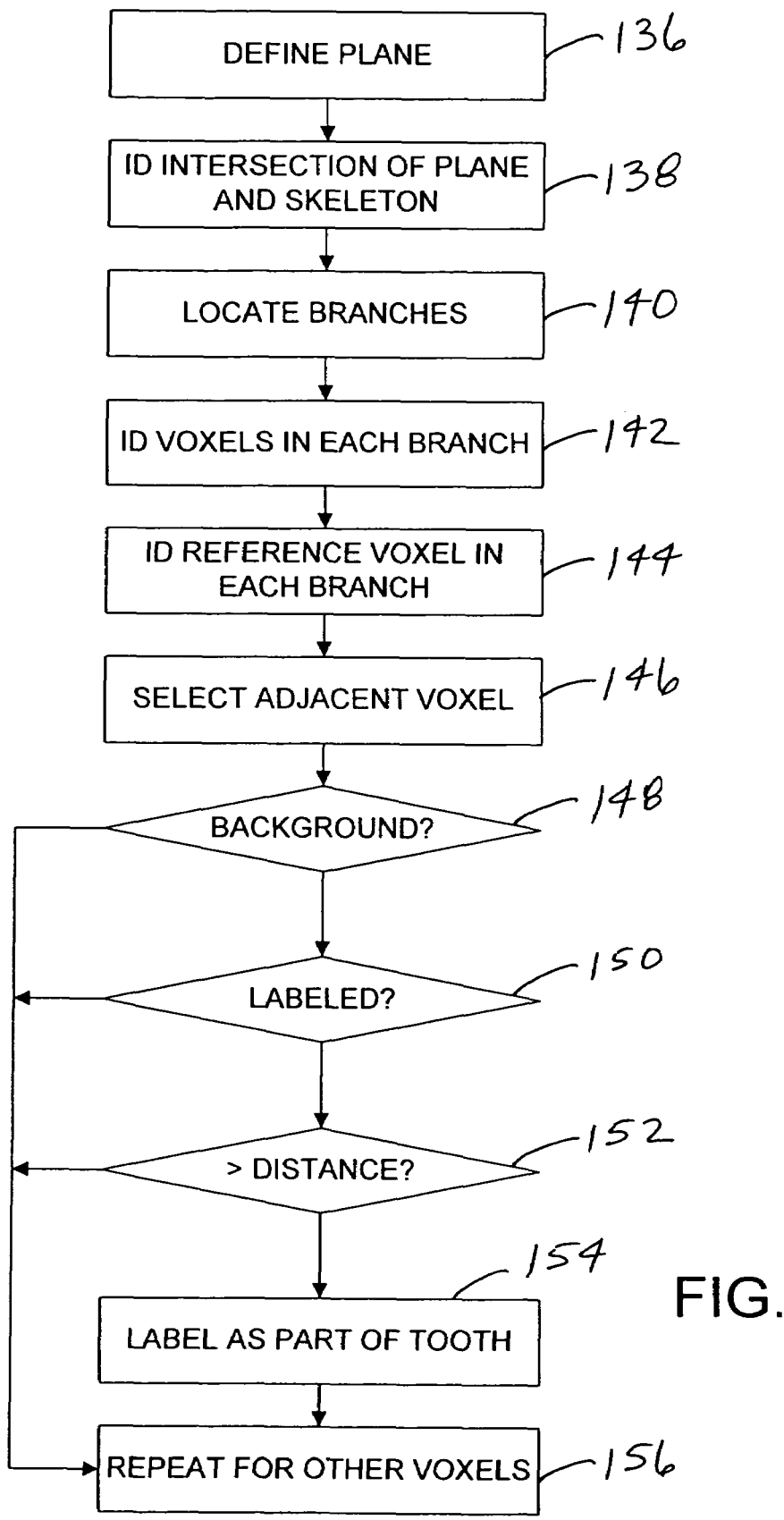

Once a skeleton has been identified, the computer uses the skeleton to divide the dentition model into 3D models of the individual teeth. FIG. 6 shows one technique for doing so. The computer first identifies those portions of the skeleton that are associated with each individual tooth. To do so, the computer defines a plane that is roughly parallel to the dentition's occlusal surface and that intersects the skeleton near its base (step 136). The computer then identifies points at which the plane and the skeleton intersect by identifying each voxel that lies on both the skeleton and the plane (step 138). In general, a single tooth includes all of the voxels that lie in a particular branch of the skeleton; and because the plane intersects the skeleton near its base, voxels that lie together in a branch of the skeleton usually cluster together on the intersecting plane. The computer is able to locate the branches by identifying voxels on the skeleton that lie within a particular distance of each other on the intersecting plane (step 140). The computer then identifies and labels all voxels on the skeleton that belong to each branch (step 142).

Once the branches are identified, the computer links other voxels in the model to the branches. The computer begins by identifying a reference voxel in each branch of the skeleton (step 144). For each reference voxel, the computer selects an adjacent voxel that does not lie on the skeleton (step 146). The computer then processes the selected voxel, determining whether the voxel lies outside of the dentition, i.e., whether the associated image value is above or below a particular threshold value (step 148); determining whether the voxel already is labeled as belonging to another tooth (step 150); and determining whether the voxel's distance measure is greater than the distance measure of the reference voxel (step 152). If none of these conditions is true, the computer labels the selected voxel as belonging to the same tooth as the reference voxel (step 154). The computer then repeats this test for all other voxels adjacent to the reference voxel (step 156). Upon testing all adjacent voxels, the computer selects one of the adjacent voxels as a new reference point, provided that the adjacent voxel is labeled as belonging to the same tooth, and then repeats the test above for each untested voxel that is adjacent to the new reference point. This process continues until all voxels in the dentition have been tested.

Figure 7A:
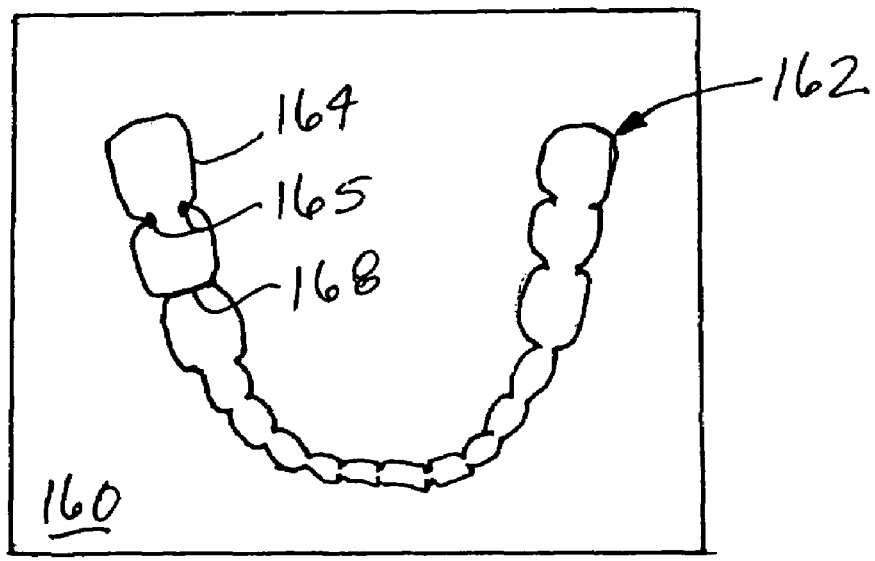
FIG. 7A is a horizontal 2D cross-sectional view of a dentition model.
Figure 7B:
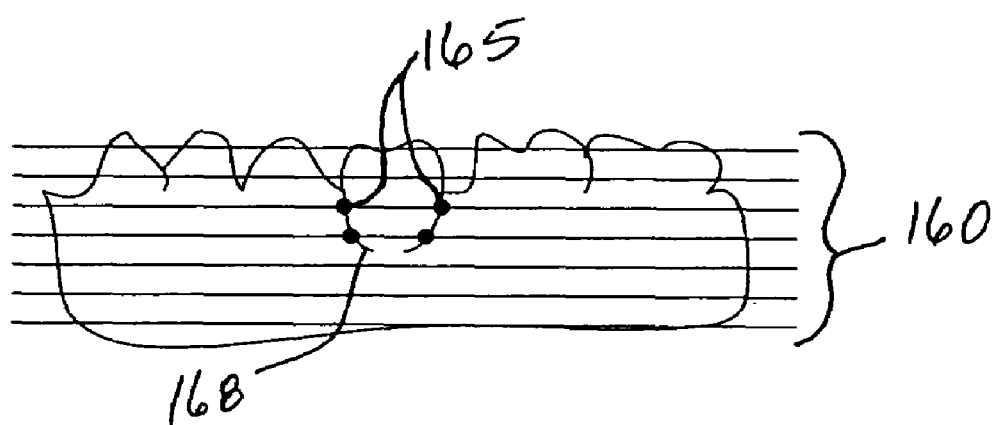
FIG. 7B is a side view of a dentition model intersected by several 2D planes.

FIGS. 7A and 7B illustrate another technique for identifying and segmenting individual teeth in the dentition model. This technique, called "2D slice analysis," involves dividing the voxel representation of the dentition model into a series of parallel 2D planes 160, or slices, that are each one voxel thick and that are roughly parallel to the dentition's occlusal plane. Each of the 2D slices 160 includes a 2D cross-section 162 of the dentition, the surface 164 of which represents the lingual and buccal surfaces of the patient's teeth and/or gums. The computer inspects the cross-section 162 in each 2D slice 160 to identify voxels that approximate the locations of the interproximal margins 166 between the teeth. These voxels lie at the tips of cusps 165 in the 2D cross-sectional surface 164. The computer then uses the identified voxels to create 3D surfaces 168 intersecting the dentition model at these locations. The computer segments the dentition model along these intersecting surfaces 168 to create individual tooth models.

Figure 8:
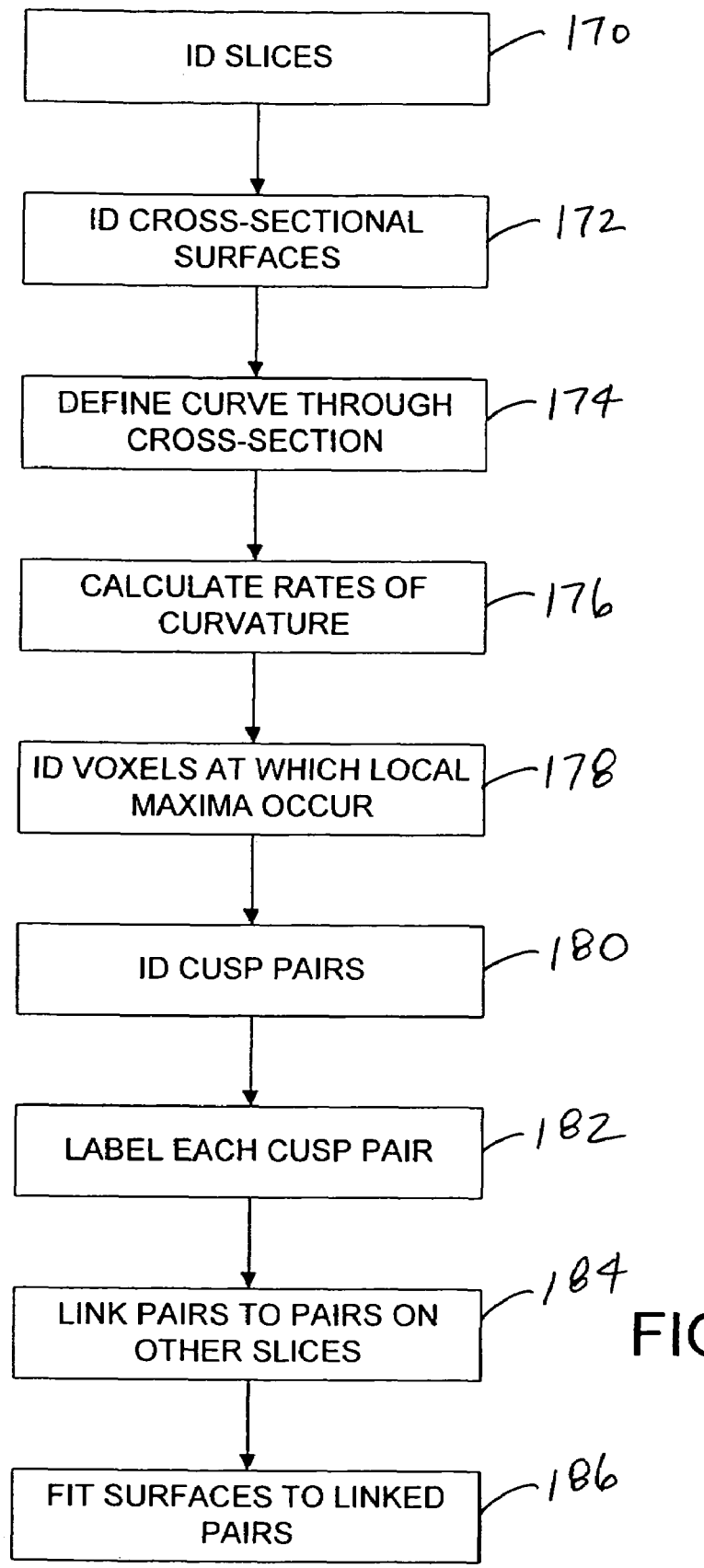
FIG. 8 is a flow diagram for a 2D slice analysis technique used in segmenting a dentition model.

FIG. 8 describes a particular implementation of the 2D slice analysis technique. The computer begins by identifying the voxels that form each of the 2D slices (step 170). The computer then identifies, for each 2D slice, the voxels that represent the buccal and lingual surfaces of the patient's teeth and gums (step 172) and defines a curve that includes all of these voxels (step 174). This curve represents the surface 164 of the 2D cross-section 162.

The computer then calculates the rate of curvature (i.e., the derivative of the radius of curvature) at each voxel on the 2D cross-sectional surface 164 (step 176) and identifies all of the voxels at which local maxima in the rate of curvature occur (step 178). Each voxel at which a local maximum occurs represents a "cusp" in the 2D cross-sectional surface 164 and roughly coincides with an interproximal margin between teeth. In each 2D slice, the computer identifies pairs of these cusp voxels that correspond to the same interproximal margin (step 180), and the computer labels each pair to identify the interproximal margin with which it is associated (step 182). The computer then identifies the voxel pairs on all of the 2D slices that represent the same interproximal margins (step 184). For each interproximal margin, the computer fits a 3D surface 168 approximating the geometry of the interproximal margin among the associated voxel pairs (step 186).

Figure 9:
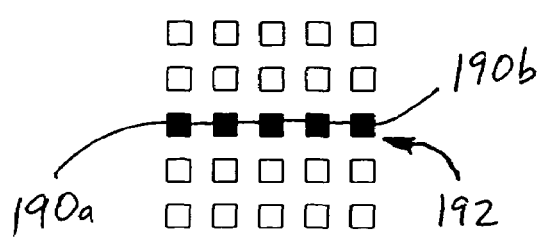
FIGS. 9 and 10A through 10C each shows a group of voxels in a 2D slice of a dentition model.

FIG. 9 illustrates one technique for creating the 3D surfaces that approximate the interproximal margins. For each pair of cusp voxels 190a–b in a 2D slice that are associated with a particular interproximal region, the computer creates a line segment 192 bounded by these cusp voxels 190a–b. The computer changes the colors of the voxels in the line segment, including the cusp voxels 190a–b that bound the segment, to contrast with the other voxels in the 2D slice. The computer creates line segments in this manner in each successive 2D slice, forming 3D surfaces that represent the interproximal regions. All of the voxels that lie between adjacent ones of these 3D surfaces represent an individual tooth.

Figure 10A:
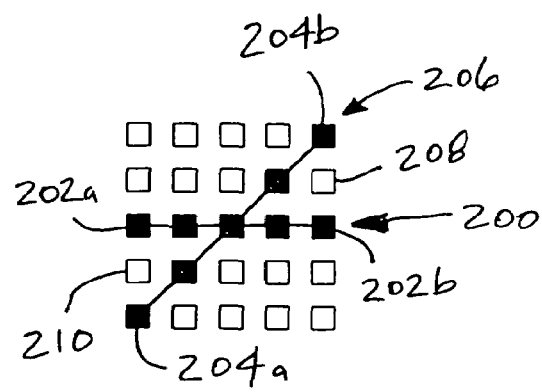
Figure 10B:
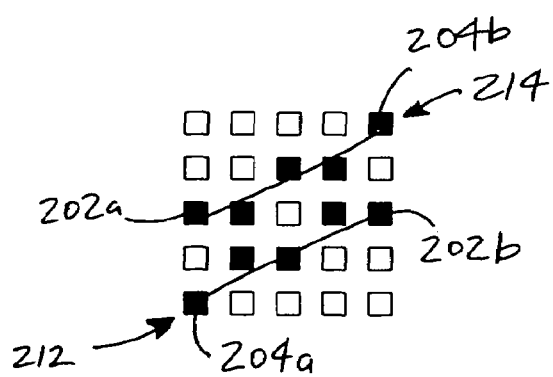
Figure 10C:
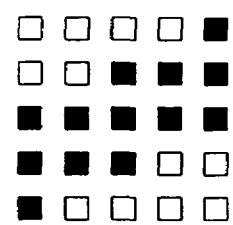

FIGS. 10A through 10C illustrate a refinement of the technique shown in FIG. 9. The refined technique involves the projection of a line segment 200 from one slice onto a line segment 206 on the next successive slice to form, for the associated interproximal margin, a 2D area bounded by the cusp voxels 202a–b, 204a–b of the line segments 200, 206. If the line segments 200, 206 are oriented such that any voxel on one segment 200 is not adjacent to a voxel on the other segment 206, as shown in FIG. 10A, then the resulting 3D surface is discontinuous, leaving unwanted "islands" of white voxels 208, 210.

The computer eliminates these discontinuities by creating two new line segments 212, 214, each of which is bounded by one cusp voxel 202a–b, 204a–b from each original line segment 200, 206, as shown in FIG. 10B. The computer then eliminates the islands between the new line segments 212, 214 by changing the colors of all voxels between the new line segments 212, 214, as shown in FIG. 10C.

Automated segmentation is enhanced through a technique known as "seed cusp detection." The term "seed cusp" refers to a location at which an interproximal margin meets the patient's gum tissue. In a volumetric representation of the patient's dentition, a seed cusp for a particular interproximal margin is found at the cusp voxel that lies closest to the gumline. By applying the seed cusp detection technique of the 2D slice analysis, the computer is able to identify all of the seed cusp voxels in the 3D model automatically.

Figure 11:
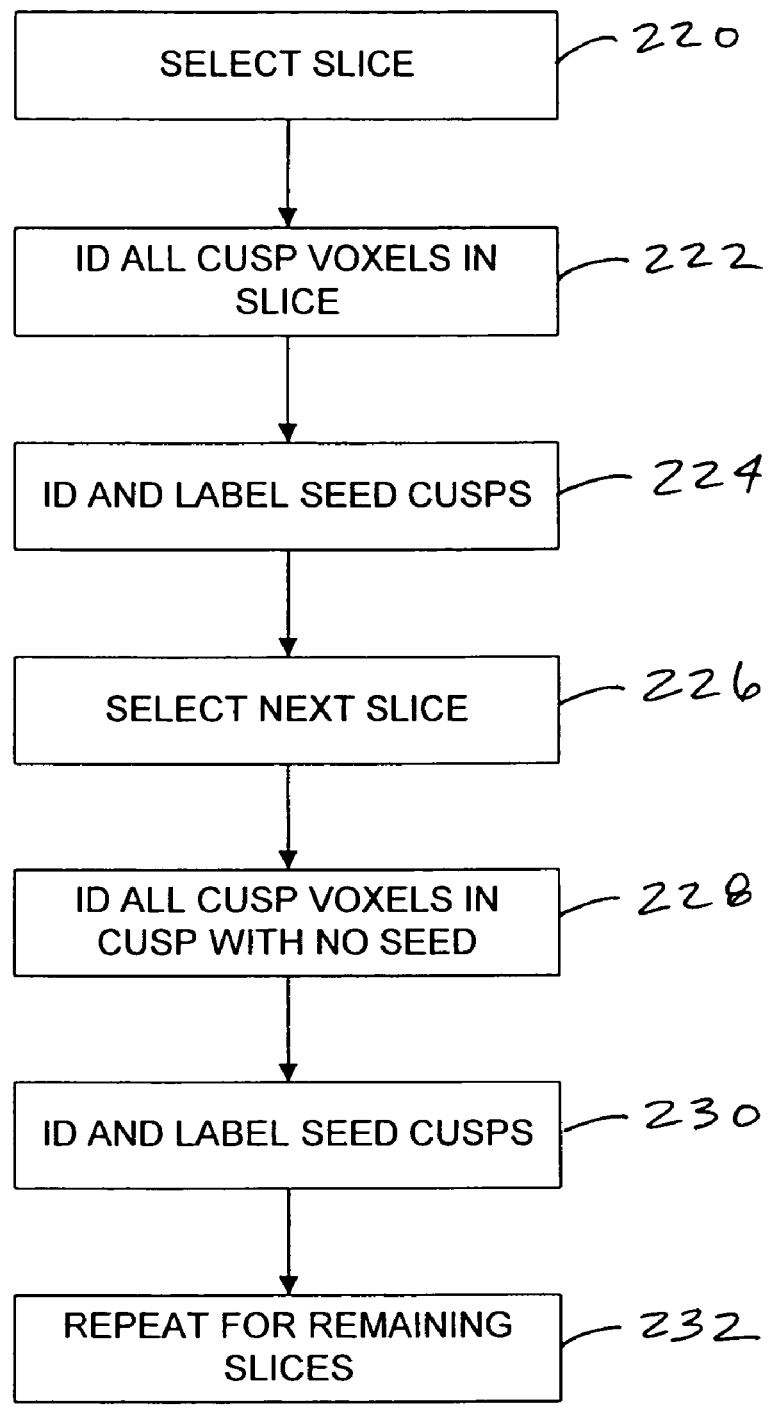
FIG. 11 is a flow chart for an automatic cusp detection technique used in segmenting a dentition model.

FIG. 11 shows a particular implementation of the seed cusp detection technique, in which the computer detects the seed cusps by identifying each 2D slice in which the rate of curvature of a cusp first falls below a predetermined threshold value. The computer begins by selecting a 2D slice that intersects all of the teeth in the arch (step 220). The computer attempts to select a slice that is near the gingival regions but that does not include any voxels representing gingival tissue. The computer then identifies all of the cusp voxels in the 2D slice (step 222). If the rate of curvature of the 2D cross-section at any of the cusp voxels is less than a predetermined threshold value, the computer labels that voxel as a seed cusp (step 224). The computer then selects the next 2D slice, which is one voxel layer closer to the gingival region (step 226), and identifies all of the cusp voxels that are not associated with a cusp for which the computer has already identified a seed cusp (step 228). If the rate of curvature of the 2D cross-section is less than the predetermined threshold value at any of these cusp voxels, the computer labels the voxel as a seed cusp (step 230) and proceeds to the next 2D slice. The computer continues in this manner until a seed cusp voxel has been identified for each cusp associated with an interproximal margin (step 232).

Figure 12:
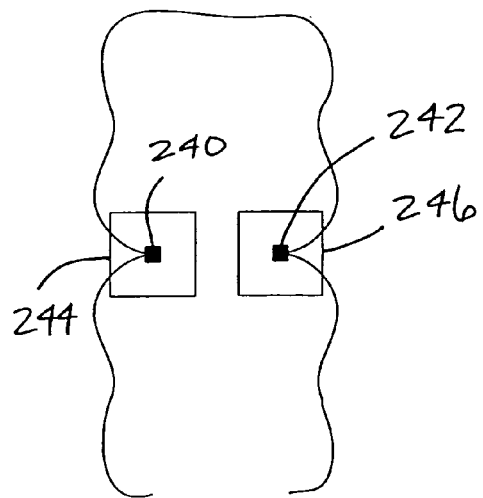
FIG. 12 is a horizontal 2D cross-section of a dentition model illustrating a neighborhood filtered automatic cusp detection technique used in segmenting the dentition model.
Figure 13:
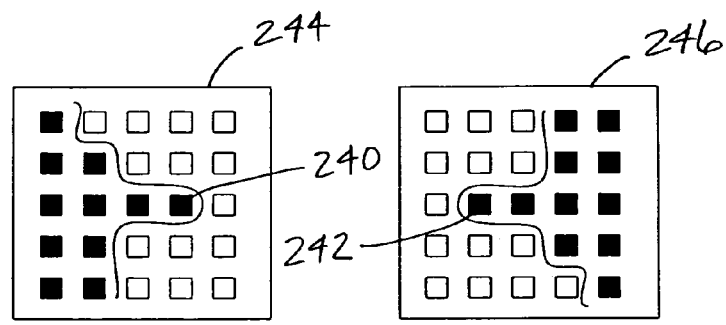
FIG. 13 is shows two groups of voxels in a 2D slice of a dentition model illustrating the neighborhood filtered automatic cusp detection technique.
Figure 14:
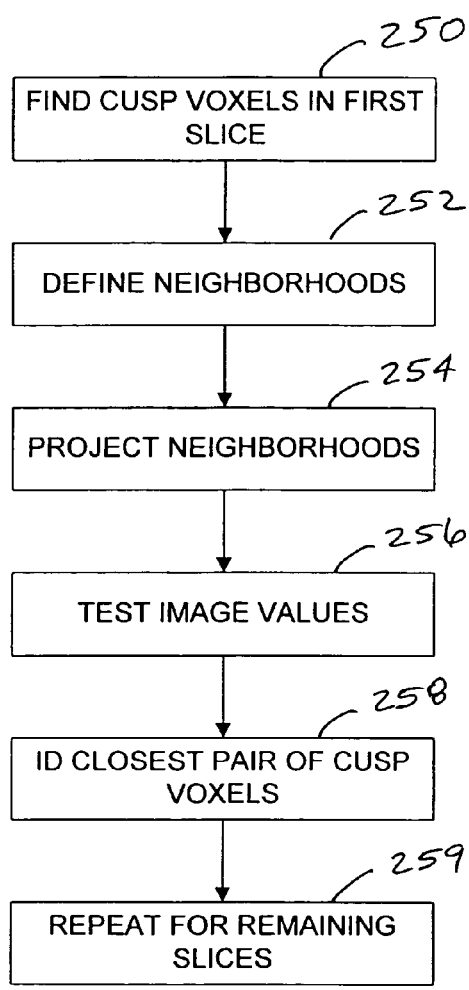
FIG. 14 is a flow chart for the neighborhood filtered automatic cusp detection technique.

FIGS. 12, 13, and 14 illustrate a technique, known as "neighborhood-filtered cusp detection," by which the computer focuses its search for cusps on one 2D slice to neighborhoods 244, 246 of voxels defined by a pair of previously detected cusp voxels 240, 242 on another 2D slice. Upon detecting a pair of cusp voxels 240, 242 in a 2D slice at level N (step 250), the computer defines one or more neighborhoods 244, 246 that include a predetermined number of voxels surrounding the pair (step 252). The computer then projects the neighborhoods onto the next 2D slice at level N+1 by identifying the voxels on the next slice that are immediately adjacent the voxels in the neighborhoods on the original slice (step 254). The neighborhoods are made large enough to ensure that they include the cusp voxels on the N+1 slice. In the example of FIG. 13, each cusp voxel 240, 242 lies at the center of a neighborhood 244, 246 of twenty-five voxels arranged in a 5×5 square.

In searching for the cusp voxels on the N+1 slice, the computer tests the image values for all voxels in the projected neighborhoods to identify those associated with the background image and those associated with the dentition (step 256). In the illustrated example, voxels in the background are black and voxels in the dentition are white. The computer identifies the cusp voxels on the N+1 slice by locating the pair of black voxels in the two neighborhoods that lie closest together (step 258). The computer then repeats this process for all remaining slices (step 259).

Figure 15:
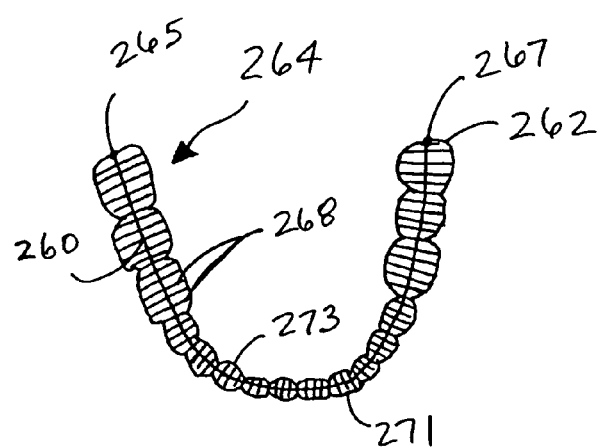
FIG. 15 is a horizontal 2D cross-section of a dentition model illustrating an arch curve fitting technique used in segmenting the dentition model.
Figure 16:
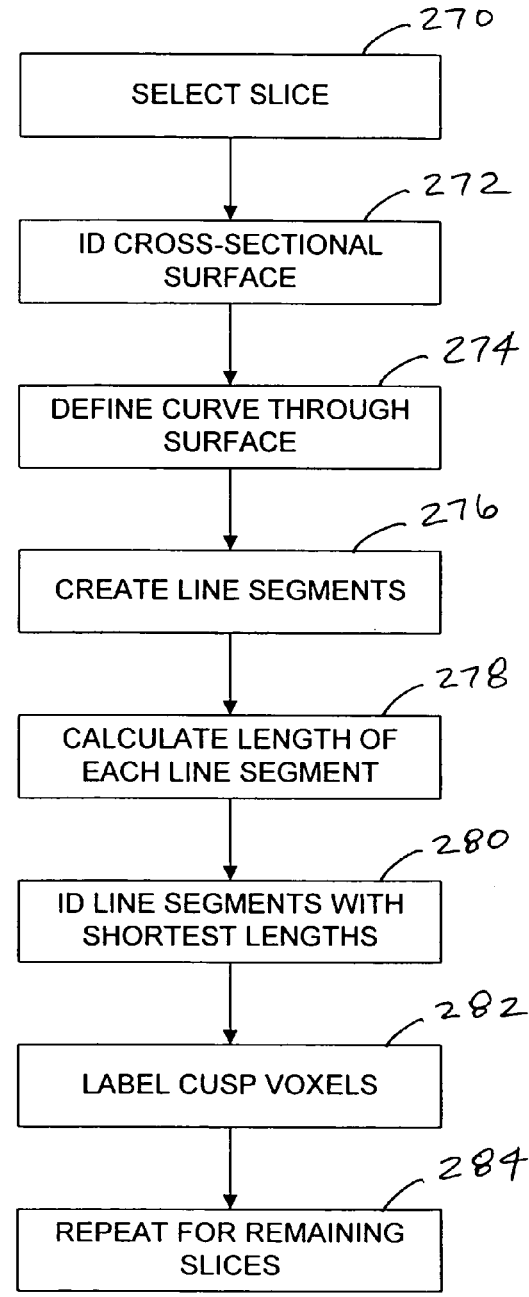
FIG. 16 is a flow chart for the arch curve fitting technique.

FIGS. 15 and 16 illustrate another technique, known as "arch curve fitting," for identifying interproximal margins between teeth in the dentition. The arch curve fitting technique, which also applies to 2D cross-sectional slices of the dentition, involves the creation of a curve 260 that fits among the voxels on the 2D cross-sectional surface 262 of the dentition arch 264. A series of closely-spaced line segments 268, each bounded by the cross-sectional surface 268, are formed along the curve 260, roughly perpendicular to the curve 260, throughout the 2D cross-section 264. In general, the shortest of these line segments 268 lie on or near the interproximal margins; thus computer identifies the cusps that define the interproximal margins by determining the relative lengths of the line segments 268.

When applying the arch curve fitting technique, the computer begins by selecting a 2D slice (step 270) and identifying the voxels associated with the surface 262 of the cross-sectional arch 264 (step 272). The computer then defines a curve 260 that fits among the voxels on the surface 262 of the arch (step 274). The computer creates the curve using any of a variety of techniques, a few of which are discussed below. The computer then creates a series of line segments that are roughly perpendicular to the curve and are bounded by the cross-sectional surface 262 (step 276). The line segments are approximately evenly spaced with a spacing distance that depends upon the required resolution and the acceptable computing time. Greater resolution leads to more line segments and thus greater computing time. In general, a spacing on the order of 0.4 mm is sufficient in the initial pass of the arch curve fitting technique.

The computer calculates the length of each line segment (step 278) and then identifies those line segments that form local minima in length (step 280). These line segments roughly approximate the locations of the interproximal boundaries, and the computer labels the voxels that bound these segments as cusp voxels (step 282). The computer repeats this process for each of the 2D slices (step 284) and then uses the cusp voxels to define 3D cutting surfaces that approximate the interproximal margins.

In some implementations, the computer refines the arch cusp determination by creating several additional sets of line segments, each centered around the arch cusps identified on the first pass. The line segments are spaced more narrowly on this pass to provide greater resolution in identifying the actual positions of the arch cusps.

The computer uses any of a variety of curve fitting techniques to create the curve through the arch. One technique involves the creation of a catenary curve with endpoints lying at the two ends 265, 267 (FIG. 15) of the arch. The catenary curve is defined by the equation y=a+b·cosh (cx), and the computer fits the curve to the arch by selecting appropriate values for the constants a, b, and c. Another technique involves the creation of two curves, one fitted among voxels lying on the front surface 271 of the arch, and the other fitted among voxels on the rear surface 273. A third curve, which guides the placement of the line segments above, passes through the middle of the area lying between the first two curves.

Figure 17:
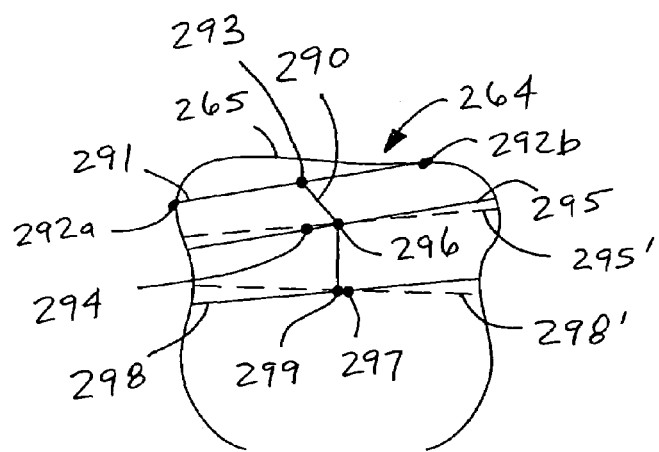
FIG. 17 is a horizontal 2D cross-section of a dentition model illustrating a curve creation technique for use with the arch curve fitting technique.
Figure 18:
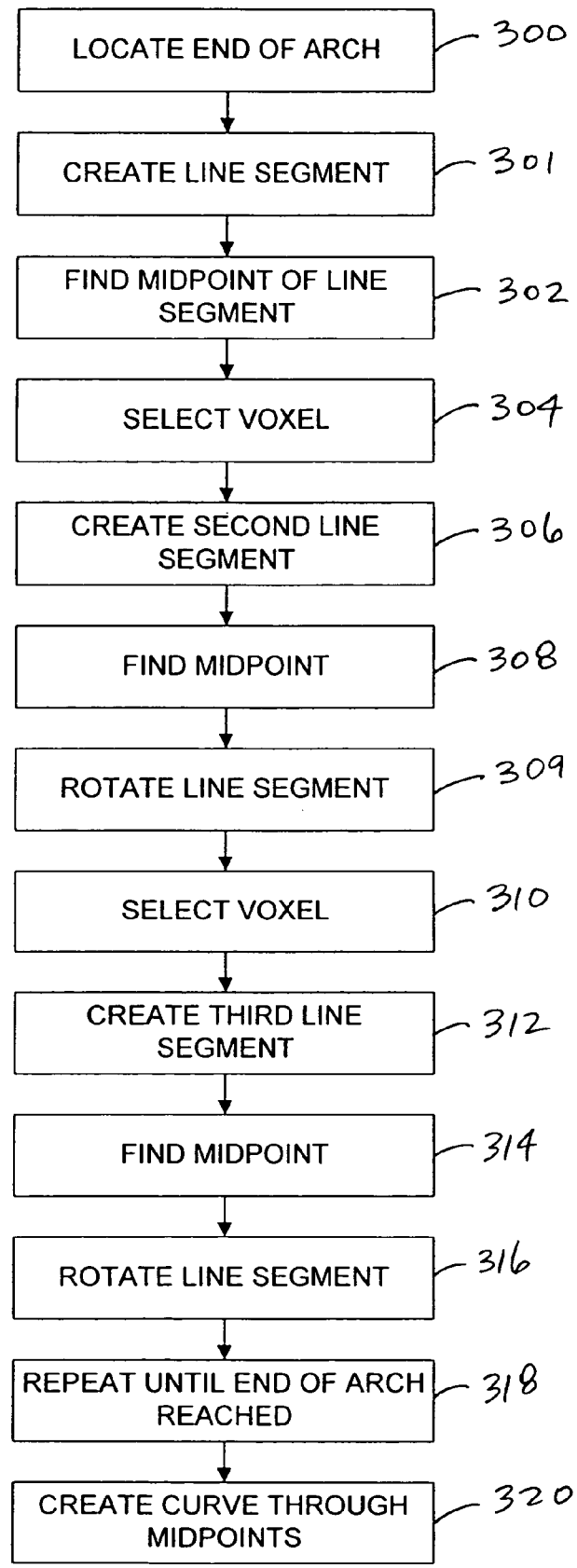
FIG. 18 is a flow diagram for the curve creation technique.

FIGS. 17 and 18 illustrate another technique for constructing a curve through the arch. This technique involves the creation of a series of initial line segments through the arch 264 and the subsequent formation of a curve 290 fitted among the midpoints of these line segments This curve 290 serves as the arch curve in the arch curve fitting technique described above.

In applying this technique, the computer first locates an end 265 of the arch (step 300) and creates a line segment 291 that passes through the arch 264 near this end 265 (step 301). The line segment 291 is bounded by voxels 292a–b lying on the surface of the arch. The computer then determines the midpoint 293 of the line segment 291 (step 302), selects a voxel 294 located particular distance from the midpoint 293 (step 304), and creates a second line segment 295 that is parallel to the initial line segment 291 and that includes the selected voxel 294 (step 306). The computer then calculates the midpoint 296 of the second segment 295 (step 308) and rotates the second segment 295 to the orientation 295' that gives the segment its minimum possible length (step 309). In some cases, the computer limits the second segment 295 to a predetermined amount of rotation (e.g., ±10°).

The computer then selects a voxel 297 located a particular distance from the midpoint 296 of the second segment 295 (step 310) and creates a third line segment 298 that is parallel to the second line segment 295 and that includes the selected voxel 297 (step 312). The computer calculates the midpoint 299 of the third segment 298 (step 314) and rotates the segment 298 to the orientation 298' that gives the segment its shortest possible length (step 316). The computer continues adding line segments in this manner until the other end of the cross-sectional arch is reached (step 318). The computer then creates a curve that fits among the midpoints of the line segments (step 320) and uses this curve in applying the arch fitting technique described above.

Figures 19A, 19B:
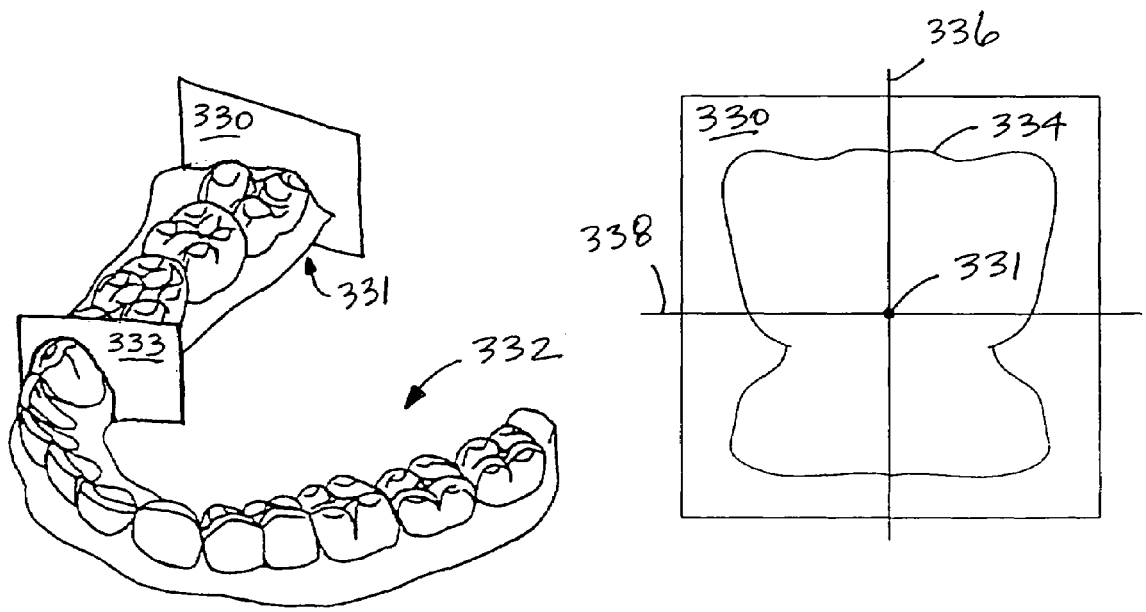
FIGS. 19A and 19B are a perspective view and a vertical 2D cross-sectional view of a dentition model illustrating another technique for use in segmenting the dentition model.
Figure 20:
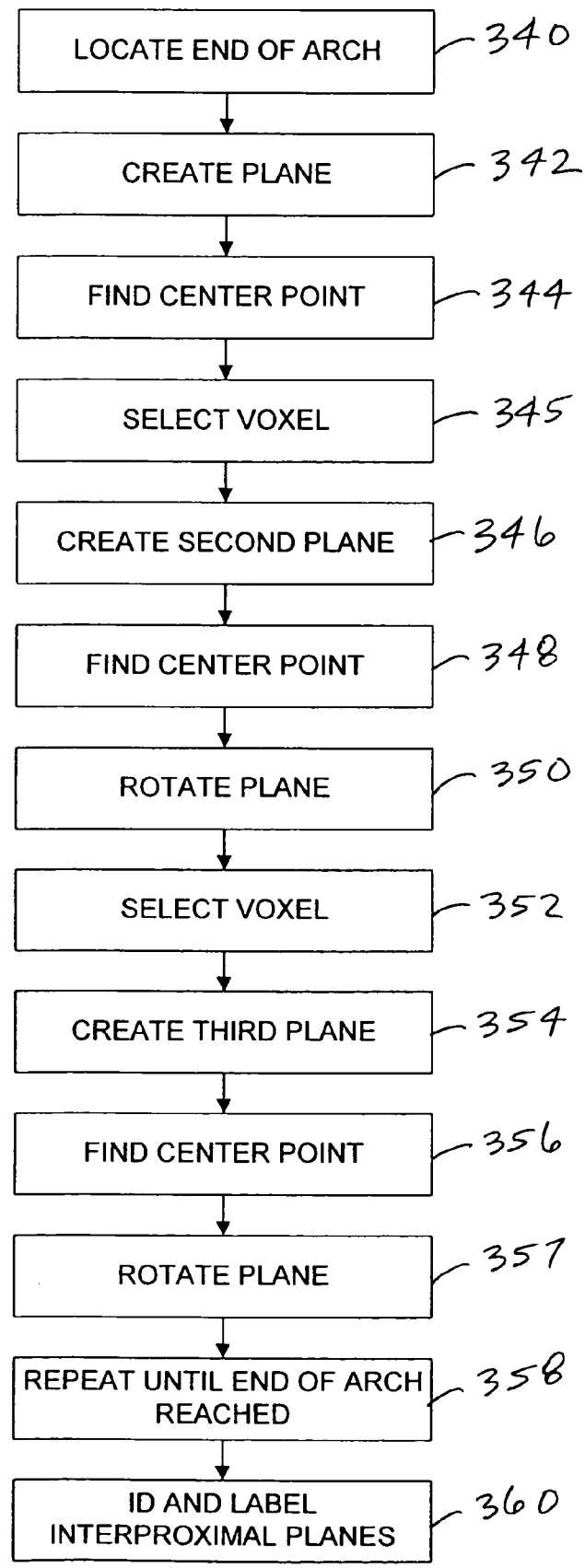
FIGS. 20 and 21 are flow diagrams of this technique.

FIGS. 19A, 19B and 20 illustrate an alternative technique for creating 3D surfaces that approximate the geometries and locations of the interproximal margins in the patient's dentition. This technique involves the creation of 2D planes that intersect the 3D dentition model at locations that approximate the interproximal margins. In general, the computer defines a series of planes, beginning with an initial plane 330 at one end 331 of the arch 332, that are roughly perpendicular to the occlusal plane of the dentition model ("vertical" planes). Each plane intersects the dentition model to form a 2D cross-section 334. If the planes are spaced sufficiently close to each other, the planes with the smallest cross-sectional areas approximate the locations of the interproximal margins in the dentition. The computer locates the interproximal regions more precisely by rotating each plane about two orthogonal axes 336, 338 until the plane reaches the orientation that yields the smallest possible cross-sectional area.

In one implementation of this technique, the computer first identifies one end of the arch in the dentition model (step 340). The computer then creates a vertical plane 330 through the arch near this end (step 342) and identifies the centerpoint 331 of the plane 330 (step 344). The computer then selects a voxel located a predetermined distance from the centerpoint (step 345) and creates a second plane 333 that is parallel to the initial plane and that includes the selected voxel (step 346). The computer calculates the midpoint of the second plane (step 348) and rotates the second plane about two orthogonal axes that intersect at the midpoint (step 350). The computer stops rotating the plane upon finding the orientation that yields the minimum cross-sectional area. In some cases, the computer limits the plane to a predetermined amount of rotation (e.g., ±10° about each axis). The computer then selects a voxel located a particular distance from the midpoint of the second plane (step 352) and creates a third plane that is parallel to the second plane and that includes the selected voxel (step 354). The computer calculates the midpoint of the third plane (step 356) and rotates the plane to the orientation that yields the smallest possible cross-sectional area (step 357). The computer continues adding and rotating planes in this manner until the other end of the arch is reached (step 358). The computer identifies the planes at which local minima in cross-sectional area occur and labels these planes as "interproximal planes," which approximate the locations of the interproximal margins (step 360).

Figure 21:
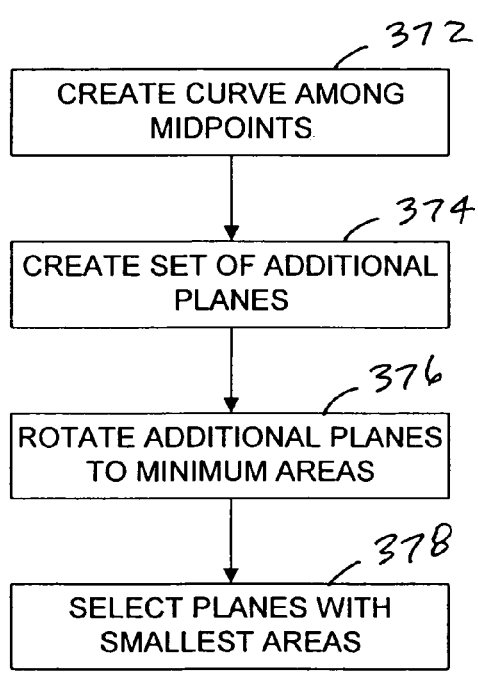

One variation of this technique, described in FIG. 21, allows the computer to refine its identification of interproximal planes by creating additional, more closely positioned planes in areas around the planes labeled as interproximal. The computer first creates a curve that fits among the midpoints of the planes labeled as interproximal planes (step 372) and then creates a set of additional planes along this curve (step 374). The additional planes are not evenly spaced along the curve, but rather are concentrated around the interproximal margins. The planes in each interproximal area are spaced very closely (e.g., 0.05 mm from each other). The computer rotates each of the newly constructed planes about two orthogonal axes until the plane reaches its minimum cross-sectional area (step 376). The computer then selects the plane in each cluster with the smallest cross-sectional area as the plane that most closely approximates the interproximal margin (step 378).

Figure 24:
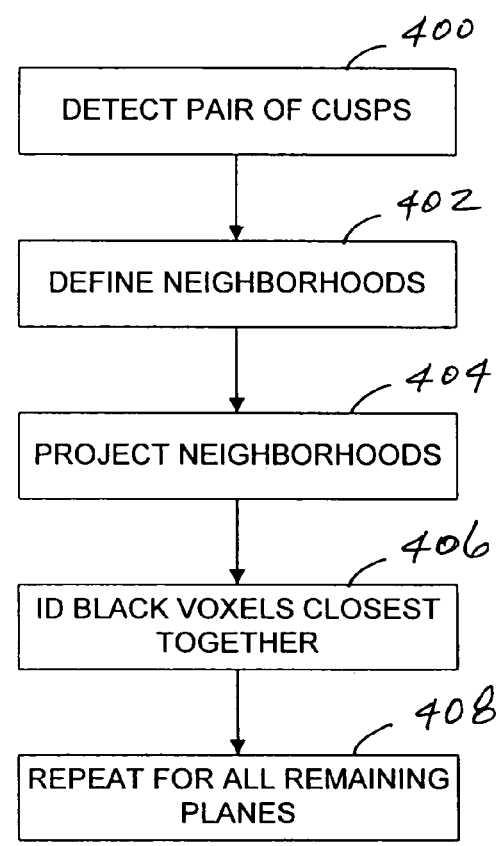
FIG. 24 is a flow diagram for the gingival margin detection technique.
Figure 22:
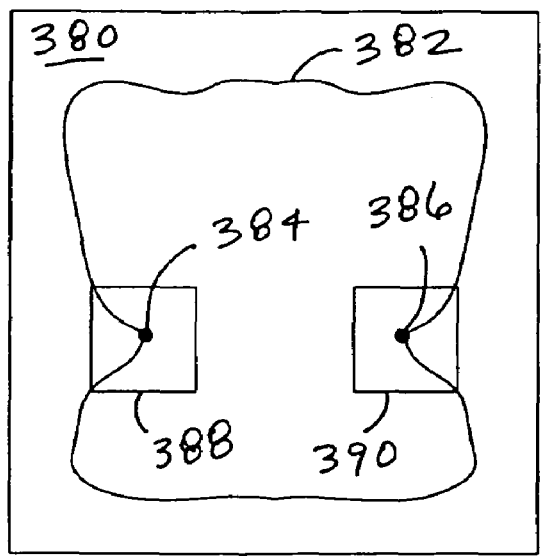
FIG. 22 is a vertical 2D cross-sectional view of a dentition model illustrating a gingival margin detection technique for use in segmenting the dentition model.
Figure 23:
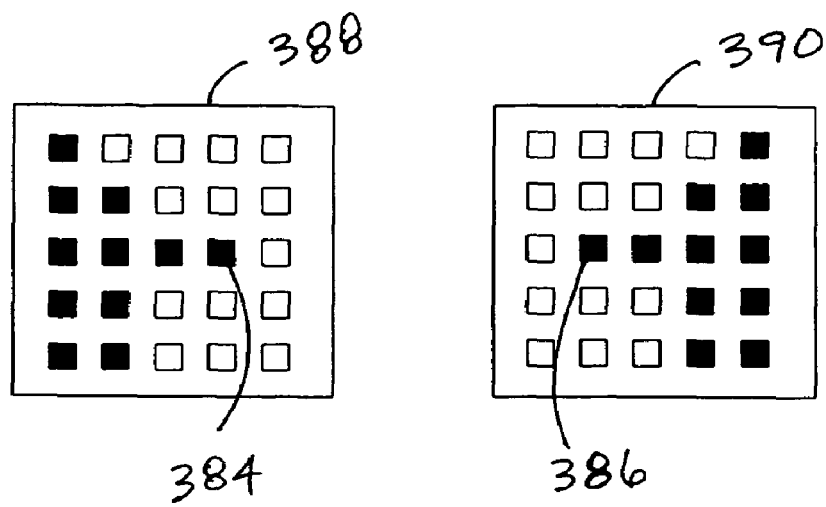
FIG. 23 shows a group of voxels in a 2D slice of a dentition model illustrating a gingival margin detection technique.

FIGS. 22, 23, and 24 illustrate a technique for identifying the gingival margin that defines the boundary between tooth and gum in the patient's dentition. This technique involves the creation of a series of horizontal 2D planes 380, or slices, that intersect the dentition model roughly perpendicular to the occlusal plane (see FIG. 19A). The cross-sectional surface 382 of the dentition model in each of these planes 380 includes cusps 384, 386 that represent the gingival margin. The computer identifies the gingival margin by applying one or more of the cusp detection techniques described above.

One technique is very similar to the neighborhood filtered cusp detection technique described above, in that voxel neighborhoods 388, 390 are defined on one of the 2D planes to focus the computer's search for cusps on an adjacent 2D plane. Upon detecting a pair of cusps 384, 386 on one 2D plane (step 400), the computer defines one or more neighborhoods 388, 390 to include a predetermined number of voxels surrounding the pair (step 402). The computer projects the neighborhoods onto an adjacent 2D plane by identifying the voxels on the adjacent plane that correspond to the voxels in the neighborhoods 388, 390 on the original plane (step 404). The computer then identifies the pair of black voxels that lie closest together in the two neighborhoods on the adjacent plane, labeling these voxels as lying in the cusp (step 406). The computer repeats this process for all remaining planes (step 408).

Many of these automated segmentation techniques are even more useful and efficient when used in conjunction with human-assisted techniques. For example, techniques that rely on the identification of the interproximal or gingival margins function more quickly and effectively when a human user first highlights the interproximal or gingival cusps in a graphical representation of the dentition model. One technique for receiving this type of information from the user is by displaying a 2D or 3D representation and allowing the user to highlight individual voxels in the display. Another technique allows the user to scroll through a series of 2D cross-sectional slices, identifying those voxels that represent key features such as interproximal or gingival cusps. Some of these techniques rely on user interface tools such as cursors and bounding-box markers.

In many instances, the computer creates proposals for segmenting the dentition model and then allows the user to select the best alternative. For example, one version of the arch curve fitting technique requires the computer to create a candidate catenary or spline curve, which the user is allowed to modify by manipulating the mathematical control parameters. Other techniques involve displaying several surfaces that are candidate cutting surfaces and allowing the user to select the appropriate surfaces.

Some implementations of the invention are realized in digital electronic circuitry, such as an application specific integrated circuit (ASIC); others are realized in computer hardware, firmware, and software, or in combinations of digital circuitry and computer components. The invention is usually embodied, at least in part, as a computer program tangibly stored in a machine-readable storage device for execution by a computer processor. In these situations, methods embodying the invention are performed when the processor executes instructions organized into program modules, operating on input data and generating output. Suitable processors include general and special purpose microprocessors, which generally receive instructions and data from read-only memory and/or random access memory devices. Storage devices that are suitable for tangibly embodying computer program instructions include all forms of non-volatile memory, including semiconductor memory devices, such as EPROM, EEPROM, and flash memory devices; magnetic disks such as internal hard disks and removable disks; magneto-optical disks; and CD-ROM.

The invention has been described in terms of particular embodiments. Other embodiments are within the scope of the following claims.

What is claimed is:

1. A computer-implemented method for use in creating a digital model of a tooth in a patient's dentition, the method comprising:
   (a) receiving a three-dimensional (3D) data set representing the patient's dentition;
   (b) applying a computer-implemented test to the 3D data set to identify data elements that represent an interproximal margin between two teeth in the dentition, wherein applying the computer-implemented test includes;
   identifying elements of the data set that represent the interproximal margin, and
   labeling those data elements as belonging to the interproximal margin; and
   (c) applying another computer-implemented test to select data elements that lie on one side of the interproximal margin for inclusion in the digital model of the tooth.

2. The method of claim 1, further comprising creating a set of 2D planes that intersect the dentition roughly perpendicular to an occlusal plane of the dentition, each 2D plane including data elements that form a 2D cross-section of the dentition.

3. The method of claim 2, further comprising identifying the 2D plane with the smallest cross-sectional area.

4. The method of claim 3, further comprising rotating the 2D plane with the smallest cross-sectional area to at least one other orientation to form at least one other 2D cross-section of the dentition.

5. The method of claim 4, further comprising selecting the orientation that gives the rotated plane its smallest possible cross-sectional area.

6. The method of claim 5, further comprising identifying data elements that represent the selected orientation of the rotated plane as lying on an interproximal margin.

7. The method of claim 4, wherein the plane is rotated about two orthogonal lines passing through its center point.

8. The method of claim 3, further comprising creating a set of additional 2D planes in the vicinity of the 2D plane with the smallest cross-sectional area.

9. The method of claim 8, further comprising identifying the plane in the set of additional planes that has the smallest cross-sectional area.

10. The method of claim 9, further comprising rotating the plane with the smallest cross-sectional area to at least one other orientation to form at least one other 2D cross-section of the dentition.

11. The method of claim 10, further comprising selecting the orientation that produces the 2D cross-section with the smallest possible area.

12. The method of claim 2, wherein creating a set of 2D planes includes creating an initial plane near one end of the dentition.

13. The method of claim 12, further comprising selecting a point in the dentition that is a predetermined distance from the initial plane and creating a second plane.

14. The method of claim 13, wherein the second plane is roughly parallel to the initial plane.

15. The method of claim 13, further comprising rotating the second plane to at least one additional orientation to form at least one additional 2D cross-section of the dentition.

16. The method of claim 15, further comprising selecting the orientation that produces the 2D cross-section with the smallest cross-sectional area.

17. The method of claim 15, further comprising selecting a point that is a predetermined distance from the second plane and creating a third plane that includes the selected point.

18. The method of claim 17, further comprising rotating the third plane to at least one other orientation to create at least one additional 2D cross-section of the dentition.

19. The method of claim 17, further comprising creating additional planes, each including a point that is a predetermined distance from a preceding plane, until the other end of the dentition is reached.

20. The method of claim 19, further comprising identifying at least one plane having a local minimum in cross-sectional area.

21. The method of claim 19, further comprising identifying a centerpoint of the cross-section in each of the planes and creating a curve that fits among the identified centerpoints.

22. The method of claim 21, further comprising creating a set of additional 2D planes along the curve, where the curve is roughly normal to each of the additional planes, and where each of the additional planes is roughly perpendicular to the occlusal plane.

23. The method of claim 22, further comprising identifying at least one of the additional planes that has a local minimum in cross-sectional area.

24. A computer-implemented method for use in creating a digital model of a tooth in a patient's dentition, the method comprising:
   (a) receiving a 3D dataset representing at least a portion of the patient's dentition, including at least a portion of a tooth and gum tissue surrounding the tooth;
   (b) applying a test to the 3D dataset to identify data elements lying on a gingival boundary that occurs where the tooth and the gum tissue meet, wherein applying the computer-implemented test includes;
   identifying elements of the data set that represent the gingival boundary, and
   labeling those data elements as belonging to the gingival boundary; and
   (c) applying a test to the data elements lying on the boundary to identify other data elements representing portions of the tooth, wherein applying the test to identify data elements on the gingival boundary includes creating a series of roughly parallel 2D planes, each intersecting the dentition roughly perpendicular to an occlusal plane of the dentition, and each including data elements that represent a cross-sectional surface of the dentition.

25. The method of claim 24, wherein the cross-sectional surface in each 2D plane includes two cusps that roughly identify the locations of the gingival boundary.

* * * * *